United States Patent
Saint-Martin

(10) Patent No.: US 9,532,807 B2
(45) Date of Patent: *Jan. 3, 2017

(54) ANCHORING MEMBER WITH SAFETY RING

(71) Applicant: Stryker European Holdings I, LLC, Kalamazoo, MI (US)

(72) Inventor: Pierre Henri Saint-Martin, Merignac (FR)

(73) Assignee: Stryker European Holdings I, LLC, Kalamazoo, MI (US)

( * ) Notice: Subject to any disclaimer, the term of this patent is extended or adjusted under 35 U.S.C. 154(b) by 60 days.

This patent is subject to a terminal disclaimer.

(21) Appl. No.: 14/496,640

(22) Filed: Sep. 25, 2014

(65) Prior Publication Data

US 2015/0012046 A1 Jan. 8, 2015

Related U.S. Application Data

(63) Continuation of application No. 13/429,916, filed on Mar. 26, 2012, now Pat. No. 8,845,695, which is a
(Continued)

(30) Foreign Application Priority Data

Mar. 15, 2001 (FR) ...................... 01 03515

(51) Int. Cl.
*A61B 17/70* (2006.01)
(52) U.S. Cl.
CPC ....... *A61B 17/7002* (2013.01); *A61B 17/7037* (2013.01); *A61B 17/7032* (2013.01)
(58) Field of Classification Search
CPC ............ A61B 17/7032; A61B 17/7037; A61B 17/7035; A61B 17/683; A61B 17/7043; A61B 17/7002; A61B 17/7086; A61B 17/864; A61B 17/7034; A61B 17/8605
(Continued)

(56) References Cited

U.S. PATENT DOCUMENTS 4,413,512 A 11/1983 Zemanek, Jr.
4,719,423 A 1/1988 Vinegar et al.
(Continued)

FOREIGN PATENT DOCUMENTS

DE 197 20 782 A1 11/1998
DE 299 03 342 U1 6/1999
(Continued)

OTHER PUBLICATIONS

French Prelliminary Search Report dated Nov. 27, 2001.

*Primary Examiner* — Pedro Philogene
(74) *Attorney, Agent, or Firm* — Lerner, David, Littenberg, Krumholz & Mentlik, LLP

(57) ABSTRACT

In one embodiment, the present invention includes a spinal osteosynthesis system comprising a connector, a connector member, a ring, and a bone anchor. The connector has an upper part disposed opposite of a lower part along a central axis. The upper part has a locking element and the lower part has a curved interior surface. The connector member can extend through the upper part along an opening axis transverse to the central axis. The ring may define a solid of revolution about the central axis. At least a portion of the ring may be receivable in the lower part of the connector. The bone anchor may have a head curved for polyaxial orientation with respect to the central axis. The locking element may be advanced towards the lower part to place the head of the bone anchor in contact with the connecting member, the ring, and the connector.

20 Claims, 4 Drawing Sheets

Related U.S. Application Data continuation of application No. 12/658,838, filed on Feb. 16, 2010, now Pat. No. 8,167,916, which is a continuation of application No. 10/096,991, filed on Mar. 13, 2002, now Pat. No. 7,686,834.

(58) Field of Classification Search
USPC .............................. 606/246–279, 301–308
See application file for complete search history.

(56) References Cited

U.S. PATENT DOCUMENTS

| | | |
|---|---|---|
| 5,212,447 A | 5/1993 | Paltiel |
| 5,466,237 A | 11/1995 | Byrd, III et al. |
| 5,690,630 A | 11/1997 | Errico et al. |
| 5,879,350 A | 3/1999 | Sherman et al. |
| 5,885,286 A | 3/1999 | Sherman et al. |
| 5,891,145 A | 4/1999 | Morrison et al. |
| 6,010,503 A | 1/2000 | Richelsoph et al. |
| 6,053,917 A | 4/2000 | Sherman et al. |
| 6,074,391 A | 6/2000 | Metz-Stavenhagen et al. |
| 6,090,111 A | 7/2000 | Nichols |
| 6,280,442 B1 * | 8/2001 | Barker ............... A61B 17/7037 606/256 |
| 6,331,179 B1 | 12/2001 | Freid et al. |
| 6,402,752 B2 | 6/2002 | Schaffler-Wachter et al. |
| 6,471,705 B1 * | 10/2002 | Biedermann ...... A61B 17/7032 606/271 |
| 6,488,681 B2 * | 12/2002 | Martin ............... A61B 17/7037 606/278 |
| 6,565,565 B1 | 5/2003 | Yuan et al. |
| 6,660,004 B2 | 12/2003 | Barker et al. |
| 6,869,433 B2 * | 3/2005 | Glascott ............. A61B 17/7037 606/308 |
| 6,905,500 B2 | 6/2005 | Jeon et al. |
| 7,686,834 B2 * | 3/2010 | Saint Martin ...... A61B 17/7037 606/264 |
| 8,167,916 B2 | 5/2012 | Saint-Martin |

FOREIGN PATENT DOCUMENTS

| | | |
|---|---|---|
| EP | 0 613 664 A2 | 9/1994 |
| EP | 2276007 A1 | 1/2011 |
| JP | 6-296621 A | 10/1994 |
| JP | 7-59795 | 3/1995 |
| JP | 8-257035 A | 10/1996 |
| JP | 11-318933 A | 11/1999 |
| WO | 96/12976 A1 | 5/1996 |
| WO | 98/27884 A1 | 7/1998 |
| WO | 99/65415 A1 | 12/1999 |
| WO | 01/15612 A1 | 3/2001 |

* cited by examiner

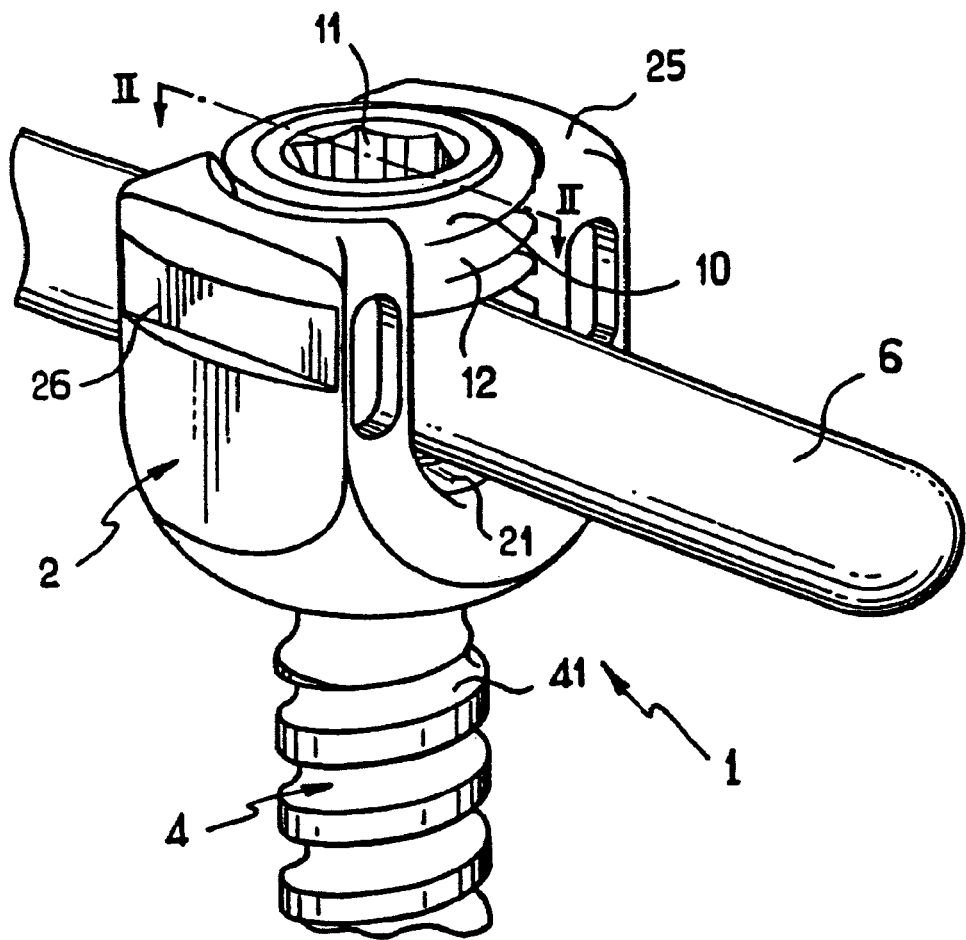
FIG_1
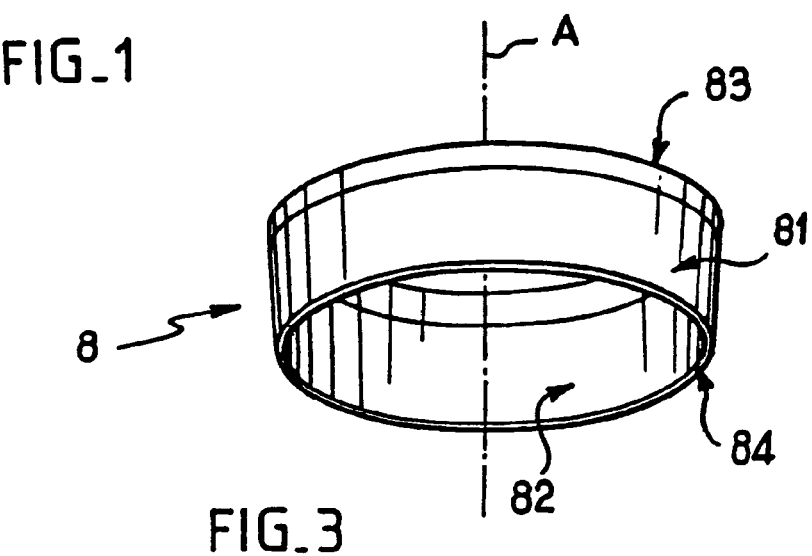
FIG_3

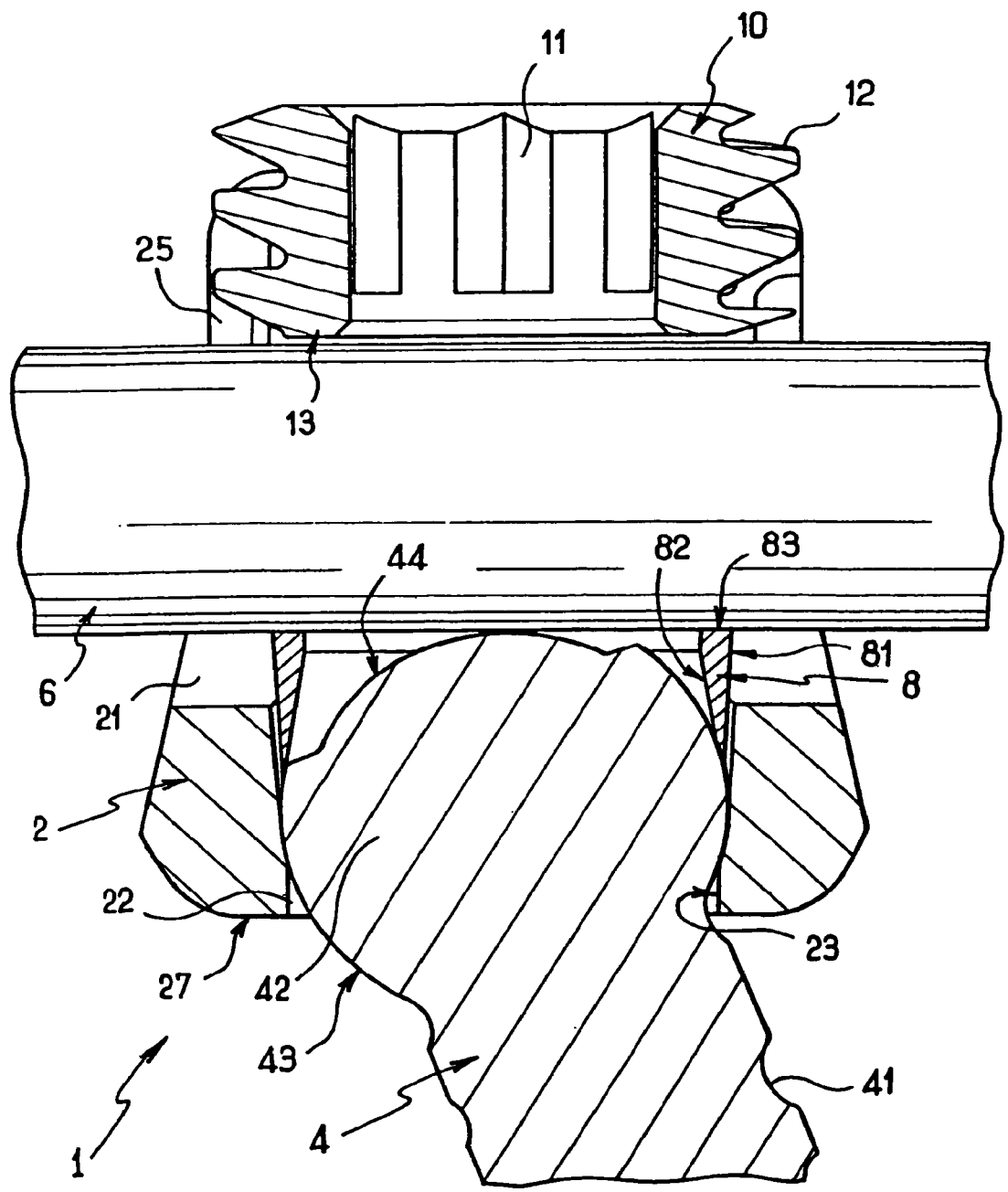
FIG_2

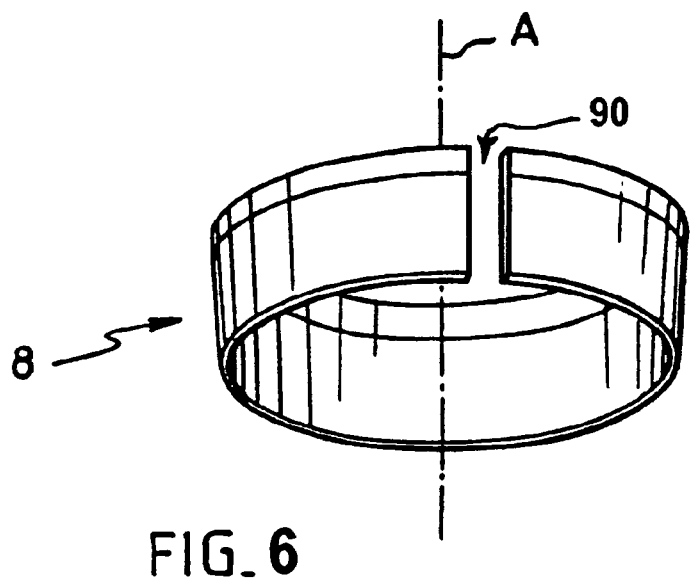
FIG_6
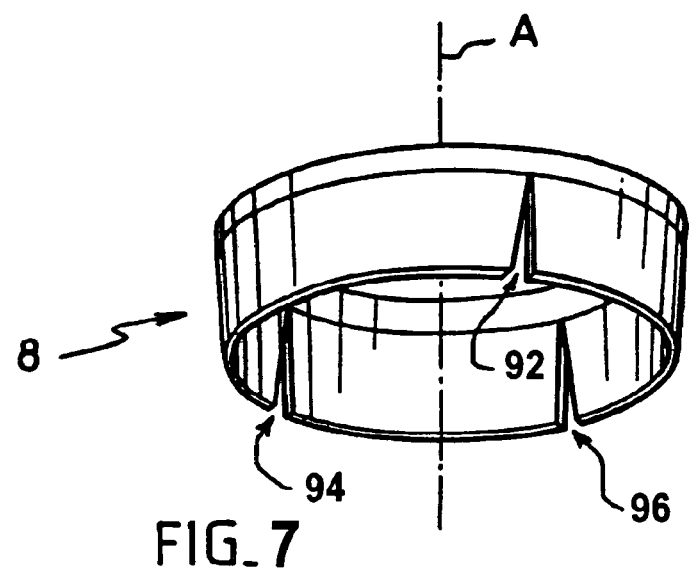
FIG_7

ANCHORING MEMBER WITH SAFETY RING

CROSS REFERENCE TO RELATED APPLICATIONS

The present application is a continuation of application Ser. No. 13/429,916, filed Mar. 26, 2012, which is a continuation of application Ser. No. 12/658,838, filed Feb. 16, 2010, which is a continuation of application Ser. No. 10/096,991, filed Mar. 13, 2002, the disclosures of which are incorporated by reference herein.

BACKGROUND OF THE INVENTION

The invention relates to osteosynthesis systems particularly for surgery on the spinal column.

SUMMARY OF THE INVENTION

Document WO 98/12 976 discloses a spinal osteosynthesis system comprising an anchoring member of the polyaxial screw type which is immobilized in position by the link rod bearing against a crown, the rounded lower surface of which bears in a complementary manner on the spherical head of the bone screw lodged in the bottom of a housing made in a connector. Such a system involves a very high bearing force between the rod and the crown in order that the pressure per unit area between the crown and the screw head is high enough to prevent any movement of one with respect to the other, which movement would have the effect of creating instability that is detrimental to the desired osteosynthesis.

One object of the invention is to provide a position-locking device which is more reliable for the same clamping force.

To do that, an aspect of the invention provides a spinal osteosynthesis assembly comprising a connector, bone anchoring means capable of being received in the connector, a connecting member capable of being received in the connector, and a ring capable of coming into contact with the head, the connecting member being able to come to bear simultaneously against the ring and the head when the ring and the anchoring means are fitted in the connector.

Thus, when locking the osteosynthesis system, the bearing of the connecting member on the ring forces the latter to come to bear against the anchoring means to immobilize the anchoring means in position within the connector, and the simultaneous bearing of the connecting member on the anchoring means enhances the previous immobilization, making it more secure while at the same time maintaining the same clamping force for locking.

Advantageously, the ring has at least one conical face.

Advantageously, the ring has a face able to come into contact with the anchoring means.

Advantageously, the ring has a face able to come into contact with a wall of the connector.

Advantageously, the faces are coaxial.

Advantageously, the ring has a flat upper edge perpendicular to an axis of the ring and able to come into contact with the connecting member.

Advantageously, the ring has a flat lower edge perpendicular to an axis of the ring.

Advantageously, the ring is able to extend between the wall and the anchoring means when the connecting member bears as mentioned.

Advantageously, the ring is deformed when the connecting member bears as mentioned, with reference to the shape that the ring had before fitting.

Advantageously, the ring has a wall thickness which varies according to a height.

Thus, the ring has a cross section in the shape of a wedge which, when the system is locked, simply wedges between the wall of the connector and the anchoring means and this, in a simple way, will further enhance the positional immobilization.

Advantageously, the ring comprises a slot.

Advantageously, the slot is arranged in such a way that the ring forms a non-closed annulus.

Advantageously, the ring comprises a number of slots distributed uniformly about a circumference of the ring.

Advantageously, the anchoring means comprise a head having a roughly spherical face.

Advantageously, the head has a first spherical face and a second spherical face which have the same center and significantly different diameters.

Advantageously, the anchoring means form a polyaxial screw.

Advantageously, the assembly comprises a locking member able to come to bear against the connecting member.

Also provided according to the invention is an osteosynthesis system comprising an assembly exhibiting at least one of the above mentioned features.

BRIEF DESCRIPTION OF THE DRAWINGS

Other features and advantages of the invention will become apparent during the following description of a preferred embodiment. In the appended drawings:

FIG. 1 is a perspective view of the preferred embodiment of the invention;

FIG. 2 is a view: in section on II-II of the embodiment of FIG. 1;

FIG. 3 is a perspective view of the ring of the preferred embodiment;

FIG. 6 is a perspectives view of an embodiment of the ring as a non-closed annulus; and FIG. 7 is a perspective view of an embodiment of the ring with circumferential slots.

DETAILED DESCRIPTION

Figure 4:
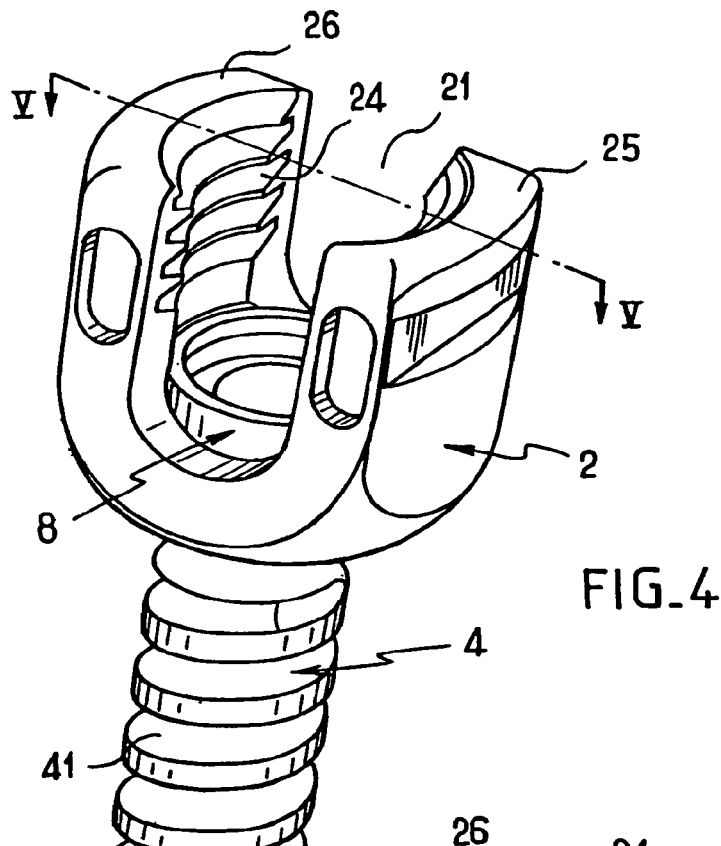
FIG. 4 is a perspective view of the embodiment of FIG. 1 prior to the fitting of the connecting member.

A preferred embodiment will be described with reference to the various FIGS. 1 to 5. The assembly for osteosynthesis of the spinal column 1 here comprises a connector 2, a connecting member 6 and anchoring means 4. Here, the connecting member 6 is an osteosynthesis rod and the anchoring means 4 are formed by a pedicle screw. The assembly 1 also comprises a ring 8 and a locking member 10 capable of locking the assembly 1 in position.

The connector 2 comprises a U-shaped opening 21 forming the upper part of the connector 2. This U-shaped opening 21 is delimited by two branches 25 and 26 which extend roughly parallel with respect to each other. The internal faces of the branches 25 and 26 which extend facing each other comprise a screw thread 24. Furthermore, the connector 2 in its lower part comprises an internal housing 22 having a wall 23. The upper part of the internal housing 22 opens into the bottom of the U-shaped opening 21 and the lower part of the internal housing 22 opens onto a lower face 27 of the connector 2. On the same side as the lower face 27, the wall 23 has a conical section designed so that the opening at the lower face 27 is smaller than the opening at the bottom of the U-shaped opening 21.

The locking member 10 comprises operating means 11 which here are in the form of a through-orifice 11 with a hexagonal socket. This hexagonal socket is designed to accommodate a hexagonal bit fitted to a screwdriver for operating it. Furthermore, the locking member 10 comprises, on its external side wall, a screw thread 12 that complements the screw thread 24 of the connector 2 between the branches 25 and 26 of which it is able to be received.

The anchoring means 4 are here in the form of a pedicle screw comprising an anchoring part 41 exhibiting a bone thread, surmounted by a head 42 which here is roughly spherical. The head 42 has a first spherical surface 43 and, forming the top, a second spherical surface 44, the diameter of which is smaller than the diameter of the spherical surface 43 but has the same center thereas.

Similar osteosynthesis systems can be found in document EP-0 613 664.

The ring 8 is of annular shape and has a first face 82 delimiting the internal wall of the ring, a second face 81 delimiting the external wall of the ring and upper 83 and lower 84 edges perpendicular to the geometric axis of revolution A of the ring 8. The faces 81 and 82 are coaxial and preferably of conical shape. Their respective generators are not mutually parallel. Thus, the faces are arranged one with respect to the other in such a way that the thickness of the ring 2 at the upper edge 83 is greater than the thickness of the ring 8 at the lower edge 84. The cross section of the ring thus has a wedge shape, giving the ring 8 a tapered shape. However, one of the generators of the faces 81 and 82 may be roughly parallel to the axis of revolution A.

Figure 5:
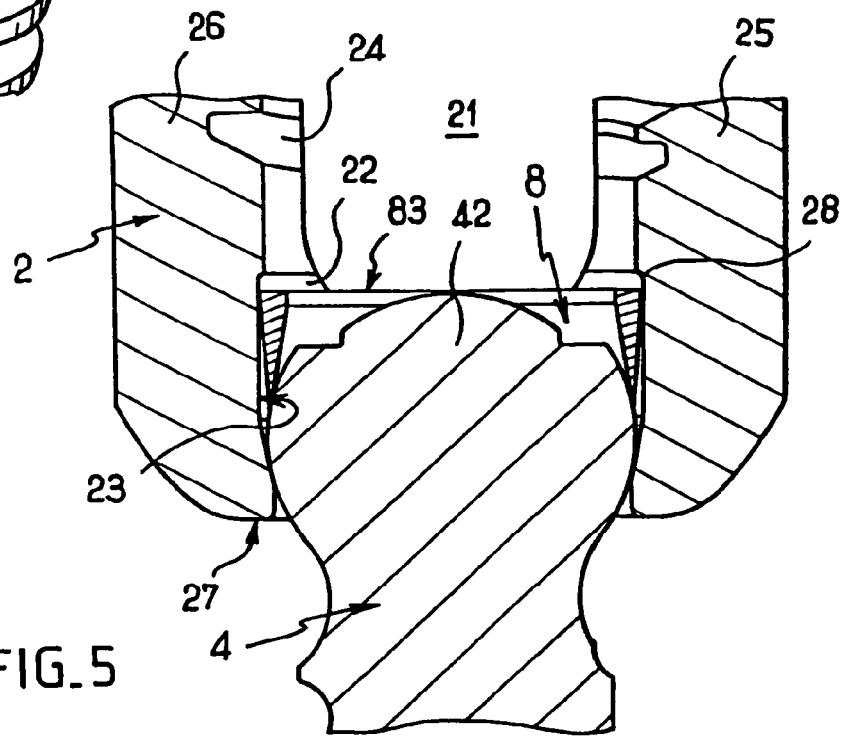
FIG. 5 is a view in section on V-V of the embodiment of FIG. 4.

Prior to use by a surgeon, the connector 2, the anchoring means 4 and the ring 8 are fitted together. More particularly, the head 42 of the anchoring means is inserted into the internal housing 22 of the connector 2. The ring 8 is then itself inserted into the internal housing 22 of the connector 2. Thus, the head 42 of the anchoring means 4 finds itself held captive in the internal housing 22 against exiting upward by the presence, inside the internal housing 22, of the ring 8, which is itself held captive, as will be seen later on. The head 42 is retained against exiting downward by the presence of the conical section of the wall 23 of the internal housing 22, which has an opening at the lower face 27 of the connector 2, the dimensions of which are smaller than the diameter of the surface 43 of the head 42. In addition, the ring 8 is held captive by retaining means 28 present within the internal housing 22. Here, the retaining means 28 stem from the difference in size between the internal housing 22 and the U-shaped opening 21, this difference forming a rim against which the upper edge 83 of the ring 8 abuts from below. This assembly is illustrated in FIGS. 4 and 5.

In use during a surgical operation, the surgeon fits an assembly as described above into the pedicle. He then fits the connecting member 6, inserting it into the U-shaped opening 21 of the connector 2. He then fits the locking member 10 between the branches 25 and 26, engaging the screw thread 12 of the locking member 10 with the complementary screw thread 24 of the connector 2. Using the hexagonal socket 11, he drives the locking member 10 so that the underside 13 of the locking member 10 comes into contact with the connecting member 6.

By continuing to screw the locking member 10 between the branches 25 and 26, the surgeon will exert a force via the locking member 10 on the connecting member 6, and this will push the connecting member 6 until the latter comes to bear against the upper edge 83 of the ring 8.

As locking continues, the ring 8 then slips along the wall 23 of the internal housing 22 until the face 82 of the ring 8 comes into contact with the surface 43 of the head 42 of the anchoring means 4. The surface 43 is itself in contact with the conical section of the wall 23 of the internal housing 22 of the connector 2. The system therefore finds itself in a situation as illustrated in FIG. 2.

During final locking, which will allow the assembly to be immobilized in position, the clamping force imparted by the surgeon via the locking member 10 will allow the ring 8 to be made to slide on the head 42. For that, the face 82 will slide on the surface 43, forcing the ring 8 to open up by deformation until the face 81 of the ring 8 comes into contact over all or part of its surface with the wall 23 of the internal housing 22 of the connector 2. At that moment, the connecting member 6 comes to bear at a point on the spherical surface 44. Thus, the head 42 is immobilized in position, on the one hand, by the ring 8 and, on the other hand, by the connecting member 6 directly. There is thus what is known as three-point contact, two of the points being diametrically opposed points of contact of the edge 83 of the ring 8 with the connecting member 6 and one additional point where the connecting member 6 contacts the surface 44 of the head 42 of the anchoring means 4.

Of course, numerous modifications could be made to the invention without departing from its scope.

For example, referring to FIG. 6, the ring 8 could have at least one slot 90. This slot could be arranged in such a way that the ring forms a non-closed annulus.

Alternately, referring to FIG. 7, the tapered shape due to the wedge shape of the cross section of the ring, instead of being continuous over its entire circumference, could consist of a number of sectors separated by slots 92, 94 and 96 to form an "umbrella" structure.

These various modifications allow easier deformation of the ring 8. This has the effect of making the ring 8 easier to introduce into the internal housing 22 of the connector 2, on the one hand, and, on the other hand, of making the final locking during use in a surgical operation easier.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A spinal osteosynthesis system comprising:
   a connector having an upper part disposed opposite of a lower part along a central axis, the upper part having a locking element and the lower part having a curved interior surface;
   a connector member extending through an opening defined through the upper part along an opening axis transverse to the central axis;
   a ring having a cross-sectional area defining a solid of revolution about the central axis, at least a portion of the ring being receivable in the lower part of the connector; and a bone anchor with a head curved for polyaxial orientation with respect to the central axis, and wherein the locking element is advanced towards the lower part to place the head of the bone anchor in contact with the connecting member, the ring, and the connector.

2. The system of claim 1, wherein the solid of revolution has an annular shape.

3. The system of claim 2, wherein the annular shape is tapered from a first end towards a second end along the central axis.

4. The system of claim 3, wherein the annular shape is tapered from an upper edge to a lower edge.

5. The system of claim 4, wherein the annular shape includes an external wall and an interior wall spanning between the upper edge and lower edges, and wherein either the external or internal wall is substantially parallel to the central axis.

6. The system of claim 5, wherein the annular shape is deformable along the central axis when the locking element is advanced towards the lower part.

7. The system of claim 6, wherein the lower edge of the annular shape defines at least one slot extending through a portion of the external and internal walls towards the upper edge.

8. The system of claim 7, wherein the at least one slot extends through the entirety of external and internal walls so that the annular shape is a split ring.

9. The system of claim 8, wherein the at least one slot has a triangular profile.

10. A spinal osteosynthesis system comprising:
a connector having an interior curve defining a first surface of revolution about the central axis;
a connector member extending through an opening in the connector along an opening axis transverse with the central axis;
an annular wedge with a cross-sectional area defining a second surface of revolution about the central axis; and
a bone anchor with a head having an exterior curve defining a third surface of revolution about the central axis,
wherein the connector and annular wedge are assembled so as to place a portion of the second surface of revolution within a portion of the first surface of revolution, and
wherein bone anchor and connector member are assembled so that application of a downward force to the connector member along the central axis places the third surface of revolution in contact with the first surface of revolution, the second surface of revolution, and the connector member.

11. The system of claim 10, wherein application of the downward force deforms the second surface of revolution against the first and third surfaces of revolution.

12. The system of claim 11, wherein the second surface of revolution has an undeformed diameter less than a maximum diameter of the third surface of revolution, and wherein the downward force deforms the second surface of revolution to have a deformed diameter greater the undeformed diameter and approximate to the maximum diameter so that the annular wedge slides at least partially over the head of the bone anchor.

13. The system of claim 12, wherein the connector member contacts the head of the bone anchor at the moment when the annular wedge slides at least partially over the head.

14. The system of claim 10, wherein the first surface of revolution is attached to an upper part of the connector with a retaining element curved about the central axis to retain a portion of the second surface of revolution within a portion of the first surface of revolution.

15. The system of claim 10, wherein the cross-sectional area of the annular wedge tapers along the central axis between an upper edge and a lower edge, and wherein application of the downward force to the upper edge positions the lower edge between the first and third surfaces of revolution.

16. A spinal osteosynthesis system comprising:
a connector having a ring retaining element adjacent to an interior curve defining a first surface of revolution about a central axis;
a connector member extending along an axis transverse with the central axis;
a ring with a triangular cross-sectional area having an upper edge and a lower edge defining a second surface of revolution about the central axis; and
a bone anchor with a head curve defining a third surface of revolution about the central axis,
wherein placing the upper edge of the ring adjacent to the ring retaining element of the connector retains a portion of the second surface of revolution within a portion of the first surface of revolution, and
wherein the bone anchor and the connector member are assembled so that application of a downward force to the connector member along the central axis places the third surface of revolution in contact with the first surface of revolution, the second surface of revolution, and the connector member.

17. The system of claim 16, wherein the third surface of revolution has a first spherical portion and a second spherical portion, the first spherical portion being offset from the second spherical portion with respect to the central axis.

18. The system of claim 17, wherein the downward force places the first spherical portion in contact with the connector member and the second spherical portion in contact with the first and second surfaces of revolution.

19. The system of claim 18, wherein the first and second spherical portion cooperatively provide the bone anchor with a polyaxial range of motion.

20. The system of claim 19, wherein the third surface of revolution remains in contact with the first surface of revolution, the second surface of revolution, and the connector member through the polyaxial range of motion of the bone anchor.

* * * * *